(12) United States Patent
Crowther et al.

(10) Patent No.: US 10,698,493 B1
(45) Date of Patent: Jun. 30, 2020

(54) VIRTUAL REALITY SURGICAL TRAINING SYSTEMS WITH ADVANCED HAPTIC FEEDBACK

(71) Applicant: FVRVS Limited, London (GB)

(72) Inventors: Ian Hew Crowther, London (GB); Victoria Jane Smalley, London (GB)

(73) Assignee: FVRVS LIMITED, London (GB)

( * ) Notice: Subject to any disclaimer, the term of this patent is extended or adjusted under 35 U.S.C. 154(b) by 0 days.

(21) Appl. No.: 16/453,877

(22) Filed: Jun. 26, 2019

(51) Int. Cl.
G09B 19/24 (2006.01)
G06F 3/01 (2006.01)
G09B 5/02 (2006.01)
G06F 3/033 (2013.01)

(52) U.S. Cl.
CPC .............. G06F 3/016 (2013.01); G06F 3/033 (2013.01); G09B 5/02 (2013.01); G09B 19/24 (2013.01)

(58) Field of Classification Search
CPC .... G09B 19/00; G09B 5/065; G09B 19/0092; G09B 5/06; G09B 5/02; G09B 19/24
USPC .......................................................... 434/267
See application file for complete search history.

(56) References Cited

U.S. PATENT DOCUMENTS

| | | | | |
|---|---|---|---|---|
| 6,113,395 A * | 9/2000 | Hon | .......... | G09B 23/28 434/262 |
| 7,121,832 B2 * | 10/2006 | Hsieh | .......... | G09B 23/28 434/262 |
| 8,306,753 B2 * | 11/2012 | Cowley | .......... | G09B 23/30 702/19 |
| 8,500,451 B2 * | 8/2013 | Bronstein | .......... | G06T 19/00 434/262 |
| 2002/0133264 A1 * | 9/2002 | Maiteh | .......... | G05B 19/4097 700/182 |
| 2006/0008786 A1 * | 1/2006 | Feygin | .......... | G09B 23/285 434/262 |
| 2007/0239409 A1 * | 10/2007 | Alan | .......... | G06F 30/23 703/2 |
| 2008/0020362 A1 * | 1/2008 | Cotin | .......... | G16H 50/50 434/267 |
| 2009/0177452 A1 * | 7/2009 | Ullrich | .......... | G06F 3/014 703/11 |
| 2010/0041004 A1 * | 2/2010 | Meglan | .......... | G09B 23/283 434/262 |
| 2010/0178644 A1 * | 7/2010 | Meglan | .......... | G06F 19/00 434/267 |
| 2010/0311028 A1 * | 12/2010 | Bell, III | .......... | G09B 23/28 434/263 |
| 2011/0117530 A1 * | 5/2011 | Albocher | .......... | G16H 50/50 434/267 |
| 2012/0059378 A1 * | 3/2012 | Farrell | .......... | A61B 17/1626 606/80 |
| 2013/0085774 A1 * | 4/2013 | Chen | .......... | G09B 23/28 705/2 |
| 2014/0057236 A1 * | 2/2014 | Meglan | .......... | G09B 23/28 434/268 |
| 2016/0210882 A1 * | 7/2016 | Gulasy | .......... | G09B 23/28 |
| 2016/0338797 A1 * | 11/2016 | Azizian | .......... | G16H 30/40 |

(Continued)

Primary Examiner — Michael C Grant
(74) Attorney, Agent, or Firm — Wilson Sonsini Goodrich & Rosati

(57) ABSTRACT

Disclosed herein are systems, methods, and software for providing a virtual environment with enhanced visual and haptic detail. In some embodiments, the haptic tool and haptic target are assigned affordance and susceptibility values, respectively, that are used to determine visual and haptic feedback.

20 Claims, 7 Drawing Sheets

(56) References Cited

U.S. PATENT DOCUMENTS

2017/0000563 A1\* 1/2017 Wang .................... A61C 19/04
2017/0108930 A1\* 4/2017 Banerjee ................ A61B 34/72
2017/0340389 A1\* 11/2017 Otto .................... A61B 5/0037

\* cited by examiner

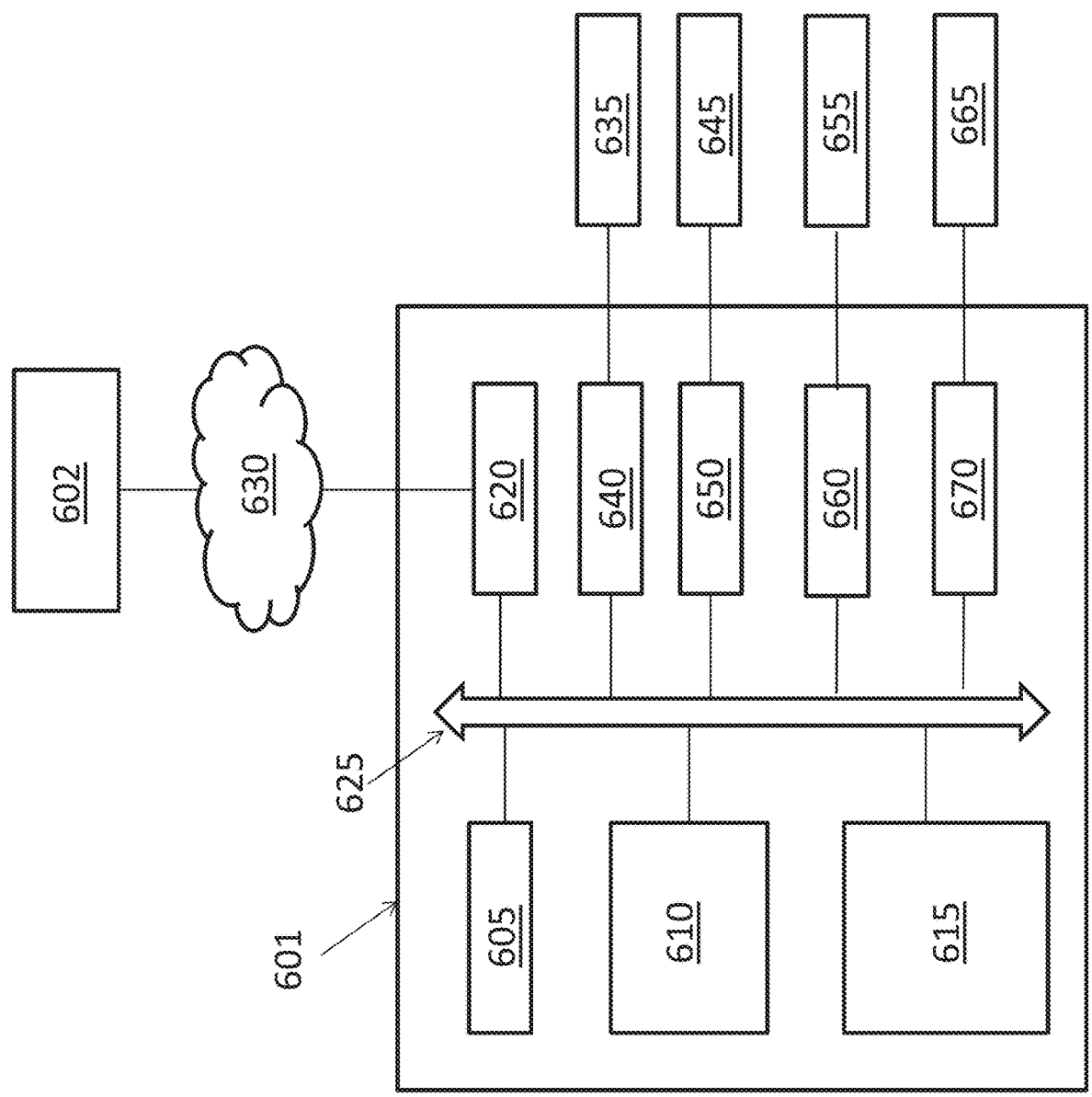

VIRTUAL REALITY SURGICAL TRAINING SYSTEMS WITH ADVANCED HAPTIC FEEDBACK

BACKGROUND

Medical training and especially surgical training involves a great deal of hands-on learning, wherein student-healthcare providers (as well as experienced healthcare providers learning new skills) are able to practice and develop skills that they need in order become proficient at medical and surgical procedures in a hands-on and immersive training environment.

SUMMARY

Described herein are systems, software, and methods for providing medical training in a cross reality (XR) environment such as, for example, a virtual, augmented, or mixed reality environment. In some embodiments, a system as described herein includes a virtual reality interface configured to provide a cross reality (XR) experience for a user (including, in some embodiments, one or more of visual, auditory, and/or tactile stimulus). In some embodiments, a system further includes at least one hand-held component used by a user to interact with an object viewed within the cross reality (XR) environment. In some embodiments, a hand-held component transmits a haptic feedback sensed by the user through the hand-held component.

Traditional medical and surgical training involve supervised direct patient interactions for healthcare providers in-training. Often times, it is the case that such training is insufficient to fully train healthcare providers in-training with respect to the procedures that they need to become facile with. This is especially the case with traditional surgical training wherein surgeons in-training are not always provided with sufficient hands-on experience in the operating room to become entirely facile with certain procedures. There is, therefore, a need to provide surgeons in-training with sufficient opportunities to have hand-on and realistic experience with surgical procedures.

To the extent that it has been possible to provide healthcare providers in-training with training modalities that utilize computer implemented methods, these methods are typically limited by current processing limitations that do not enable providing users with seamless realistic immersive training.

In contrast to traditional medical and surgical training techniques, described herein is a virtual (or augmented or mixed) reality training modality that provides a seamless virtual (or augmented or mixed) reality realistic operating room experience wherein a user is able to engage in a fully realistic computer simulated surgery.

The systems, software and methods described herein are configured to overcome limitations on existing computer implemented medical training technologies by storing data related to the virtual (or augmented or mixed) experience in a highly efficient manner that allows the handling of the interactions between tools and targets to be handled through an abstraction layer, radically reducing the amount of programming effort needed to support the required tools and targets needed to fulfil surgical simulation. In general, realistic cross reality (e.g., mixed, augmented, or virtual) experiences require processing a relatively large amount of data relatively quickly and the systems, software and methods described herein are configured to create a realistic training experience by providing an experience that includes a great deal of visual, and/or auditory, and/or tactile detail (e.g., data) that is presented seamlessly (e.g., without processing delay) to the user. Haptic details can be enhanced using a unique algorithmic process that provides a simulated, mixed, or virtual environment with dynamic haptic feedback that does not require pre-programmed interactions for each tool and target (object) combination. For example, a conventional approach to determining haptic feedback for interactions would be to specifically program each type of interaction. However, this requires programming the combination of each of these interactions on a case by case basis, which leads to a vast amount of haptic action programming and prevents true free-form engagement between the hand-held component (e.g., haptic tools) and targets (e.g., virtual objects). Moreover, the visual feedback can also be algorithmically configured to be displayed in accordance with the type of interaction. Therefore, both the visual and haptic rendering methods described herein represent improvements in the technical field of virtual simulations that incorporate unconventional data processing steps. These methods are practically integrated into virtual simulations to provide an improved and realistic experience such as, for example, in training surgical techniques.

In one aspect, disclosed herein is a computer based surgical training system, comprising (a) a processor; (b) a hand-held component operatively coupled to the processor and configured to provide a haptic feedback to a user; (c) a non-transitory computer readable storage medium encoded with a computer program that causes the processor to: (i) display a virtual object as part of a virtual surgical field, wherein the virtual object is associated with a susceptibility value; (ii) display a movement of a virtual surgical instrument within the virtual surgical field based on an input from the hand-held component when a user moves the hand-held component, wherein the virtual surgical instrument is associated with an affordance value; (iii) determine a haptic value based on the susceptibility value, the input, and the affordance value when the virtual surgical instrument is displayed in an interaction with the virtual object within the virtual surgical field; and (iv) transmit the haptic feedback to the hand-held component wherein a quantity of the haptic feedback that is transmitted is determined based on the haptic value. In some embodiments, the hand-held component comprises a wand or a joystick. In some embodiments, the hand-held component comprises a mouse or a roller. In some embodiments, the hand-held component comprises a grasper or glove. In some embodiments, the virtual object comprises a representation of at least one of a bone, a muscle, an organ, a blood vessel, blood, and a nerve. In some embodiments, the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, or a suctioning instrument. In some embodiments, the computer program further causes the processor to display a movement of the virtual surgical instrument in the surgical field in the same direction as a movement of the hand-held component based on the input. In some embodiments, the input comprises a force applied by the user to the hand-held component. In some embodiments, the force corresponds to at least one of a gripping force, a pushing force, a pulling force, or a rotational force. In some embodiments, the haptic feedback comprises a sensation that represents a response of the virtual object to the force. In some embodiments, the haptic value comprises an algorithmic calculation of the susceptibility value and the affordance value. In some embodiments, the algorithmic calculation corresponds to visual feedback comprising a visual effect on the virtual object. In some embodiments, the interaction comprises moving the object of interest with the virtual surgical instrument. In some embodiments, the interaction comprises cutting the object of interest with the virtual surgical instrument. In some embodiments, the interaction comprises applying a force to the object of interest with the virtual surgical instrument. In some embodiments, the interaction is displayed seamlessly during the period that the interaction is displayed. In some embodiments, the computer program causes the processor to: provide visual feedback corresponding to the interaction. In some embodiments, the visual feedback comprises a visual effect on the virtual object based on the susceptibility value, the input, and the affordance value. In some embodiments, the visual effect comprises a deformation, a burning, a color change or discoloration, a clean cut, a minor cut, tearing or ripping, grinding, freezing, or any combination thereof. In some embodiments, the visual effect comprises a 2-dimensional effect, a 3-dimensional effect, or both. In some embodiments, the visual feedback does not comprise a visual effect on the virtual object when an algorithmic calculation of the susceptibility value, the input, and the affordance value indicates the interaction has no effect on the virtual object. In some embodiments, the virtual object is associated with a plurality of susceptibility values. In some embodiments, each of the plurality of susceptibility values corresponds to a type of interaction. In some embodiments, the virtual surgical instrument is associated with a plurality of affordance values. In some embodiments, each of the plurality of affordance values corresponds to a type of interaction.

In another aspect, disclosed herein is a computer implemented method comprising: (a) displaying a virtual object as part of a virtual surgical field, wherein the virtual object is associated with a susceptibility value; (b) displaying a movement of a virtual surgical instrument within the virtual surgical field based on an input from a hand-held component when a user moves the hand-held component, wherein the virtual surgical instrument is associated with an affordance value; (c) determining a haptic value based on the susceptibility value, the input, and the affordance value when the virtual surgical instrument is displayed in an interaction with the virtual object within the virtual surgical field; and (d) transmitting the haptic feedback to the hand-held component wherein a quantity of the haptic feedback that is transmitted is determined based on the haptic value. In some embodiments, the hand-held component comprises a wand or a joystick. In some embodiments, the hand-held component comprises a mouse or a roller. In some embodiments, the hand-held component comprises a surgical grasper. In some embodiments, the virtual object comprises a representation of at least one of a bone, a muscle, an organ, a blood vessel, blood, and a nerve. In some embodiments, the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, or a suctioning instrument. In some embodiments, the method comprises displaying a movement of the virtual surgical instrument in the surgical field in the same direction as a movement of the hand-held component based on the input. In some embodiments, the input comprises a force applied by the user to the hand-held component. In some embodiments, the force corresponds to at least one of a gripping force, a pushing force, a pulling force, or a rotational force.

In some embodiments, the haptic feedback comprises a sensation that represents a response of the virtual object to the force. In some embodiments, the haptic value comprises an algorithmic calculation of the susceptibility value and the affordance value. In some embodiments, the algorithmic calculation corresponds to visual feedback comprising a visual effect on the virtual object. In some embodiments, the interaction comprises moving the object of interest with the virtual surgical instrument. In some embodiments, the interaction comprises cutting the object of interest with the virtual surgical instrument. In some embodiments, the interaction comprises applying a force to the object of interest with the virtual surgical instrument. In some embodiments, the interaction is displayed seamlessly during the period that the interaction is displayed In some embodiments, the method further comprises providing visual feedback corresponding to the interaction. In some embodiments, the visual feedback comprises a visual effect on the virtual object based on the susceptibility value, the input, and the affordance value. In some embodiments, the visual effect comprises a deformation, a burning, a color change or discoloration, a clean cut, a minor cut, tearing or ripping, grinding, freezing, or any combination thereof. In some embodiments, the visual effect comprises a 2-dimensional effect, a 3-dimensional effect, or both. In some embodiments, the visual feedback does not comprise a visual effect on the virtual object when an algorithmic calculation of the susceptibility value, the input, and the affordance value indicates the interaction has no effect on the virtual object. In some embodiments, the virtual object is associated with a plurality of susceptibility values. In some embodiments, each of the plurality of susceptibility values corresponds to a type of interaction. In some embodiments, the virtual surgical instrument is associated with a plurality of affordance values. In some embodiments, each of the plurality of affordance values corresponds to a type of interaction.

BRIEF DESCRIPTION OF THE DRAWINGS

The novel features of the invention are set forth with particularity in the appended claims. The file of this patent contains at least one drawing/photograph executed in color. Copies of this patent with color drawing(s)/photograph(s) will be provided by the Office upon request and payment of the necessary fee. A better understanding of the features and advantages of the present invention will be obtained by reference to the following detailed description that sets forth illustrative embodiments, in which the principles of the invention are utilized, and the accompanying drawings of which:

FIG. 6 shows exemplary embodiments of a computer system as described herein.

DETAILED DESCRIPTION

Figure 1:
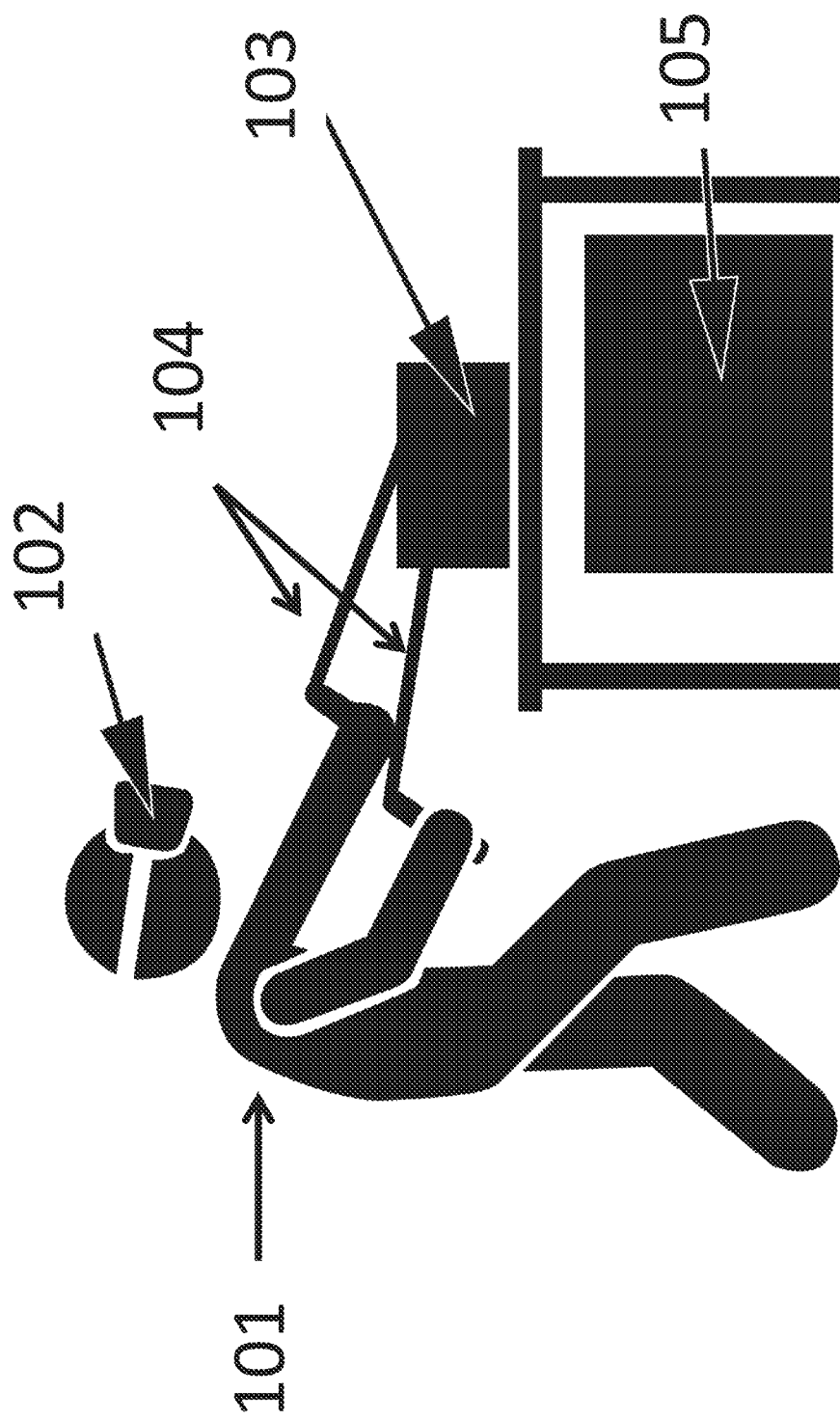
FIG. 1 illustrates an example of a user engaging a system disclosed herein.

Described herein are cross reality (XR) surgical training systems, tools, apparatuses, software, and methods for performing medical procedures in a simulated environment (e.g., virtual reality, mixed reality, or augmented reality). In some embodiments, a system described herein provides graphic simulations of a medical surgery that deliver a user realistic feedback (e.g., haptic feedback) from a computer interface tool representing a virtual surgical instrument displayed in the simulation. In some embodiments, the training system provides consistent, realistic learning experiences for surgeons, trainees, new clinicians, or students.

In some embodiments, disclosed herein is a computer based surgical training system, comprising a processor, a hand-held component operatively coupled to the processor, and a non-transitory computer readable storage medium encoded with a computer program configured to communicate with the processor. In some embodiments, the system combines a sense of presence with a unique sense of touch to create a near-real operating experience, feel, and interaction with a patient. In some embodiments, a user of the system, e.g., a surgeon or trainee, can feel the interaction with tissue and real-time feedback. In some embodiments, the system disclosed herein provides a safe, measurable and repeatable involvement with medical training in procedures including orthopedic surgery, e.g., spinal pedicle screw, total knee arthroplasty, total hip arthroplasty (posterior, or anterior), laparoscopic surgery, general surgery, cardiovascular surgery, brain or neural surgery, and otolaryngology (ear, nose, throat) surgery.

The details of one or more inventive embodiments are set forth in the accompanying drawings, the claims, and the description herein. A feature, object, or advantage of an inventive embodiment disclosed and contemplated herein can be combined with that of any other embodiment disclosed and contemplated herein, unless explicitly excluded.

Unless otherwise indicated, open terms for example "contain," "containing," "include," "including," and the like mean comprising.

The singular forms "a", "an", and "the" are used herein to include plural references unless the context clearly dictates otherwise. Accordingly, unless the contrary is indicated, the numerical parameters set forth in this application are approximations that may vary depending upon the desired properties sought to be obtained by the present invention.

Virtual Simulated Items and Environment

Disclosed herein, in some aspects, is a haptic tool that is a simulated item that can affect or interact with a second simulated item (e.g., haptic target). A haptic target is a simulated item that can be affected by a haptic tool. In some embodiments, the haptic tool evokes a haptic response from the haptic target.

Disclosed herein, in some aspects, is a virtual surgical instrument. In some embodiments, the virtual surgical instrument is a haptic tool that affects a haptic feedback on a virtual object. In some embodiments, the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof. In some embodiments, the virtual surgical instrument elicits a haptic response from the haptic target.

Disclosed herein, in some aspects, is a virtual object that can be a haptic target that is affected by a virtual surgical instrument. In some embodiments, the virtual object comprises one or more anatomical features. In some embodiments, the virtual object comprises a representation of a tissue and/or organ. In some embodiments, the virtual object comprises a representation of one or more layers or subcomponents or a tissue and/or organ. In some embodiments, the virtual object comprises a representation of at least one of a skin, cartilage, a bone, a muscle, an organ, blood, a blood vessel, tendon, and a nerve.

Disclosed herein, in some aspects, is a virtual surgical field that is a simulated environment surrounding a virtual object and/or a simulated environment within which one or more virtual objects are represented. In some embodiments, the virtual surgical field comprises an operating room or a part thereof, a screen displaying instruction or information, a diagnostic or planning image (e.g., x-ray image), a surgical tool, a microscope, a laser range finder, a camera, a surgical light, an endoscope, an ultrasound probe, a radiotherapy device, an interventional medical tool, a rehabilitative system for physical therapy, or any combination thereof. In some embodiments, the virtual surgical field comprises one or more representations of a medical personnel such as a surgeon, nurse, or assistant. In some embodiments, one or more virtual objects are provided within the simulated environment such as, for example, tissues, organs, or subjects subject to interaction using the haptic tool. In some embodiments, multiple virtual objects are provided within the simulated environment. These virtual objects can provide distinct haptic and/or visual feedback in response to user interaction through the haptic tool and display.

In some embodiments, the system provides a plurality of haptic tools for interacting with the simulated environment. In some embodiments, the system provides two haptic tools for interacting with the simulated environment. In some embodiments, the two haptic tools have the same physical configuration. In some embodiments, the two haptic tools have different physical configurations. For example, one haptic tool can be a long and thin tool corresponding to similarly shaped surgical instruments such as a scalpel, while another haptic tool can be shaped to resemble scissors. In some embodiments, the haptic tool is detachably coupled to the system to allow easy installation and/or swapping of different tools. Accordingly, different surgical simulations requiring different tools may be more realistically approximated by allowing the appropriate tools that most resemble the virtual surgical instrument to be used.

In some embodiments, the virtual surgical field comprises a navigation system that displays the positions of surgical tools with respect to pre- or intraoperative images. As a non-limiting example, in the case of a simulated virtual surgery of the spine, the virtual surgical field provides a navigation system having a computer display that shows 3D computed tomography of the spine before surgery has commenced (pre-operative image). This information helps the user plan and/or visualize the surgical operations to be performed. Next, while the surgery is ongoing, additional 3D computed tomography images are displayed (intraoperative imaging). Thus, the user is able to view images of the bony and soft tissues of the spine and the positioning of his or her surgical tools with respect to those tissues. In this way, the systems and methods disclosed herein can more accurately simulate the operating room by displaying pre- or intraoperative images within the virtual environment. In some embodiments, the navigation system comprises a display showing one or more pre- or intraoperative images. In some embodiments, the images show the position(s) of one or more surgical tools. In some embodiments, the images show the tissues that are being operated on or will be operated on during the virtual simulation. In some embodiments, these images include intraoperative images, such as two-dimensional fluoroscopic images, and preoperative three dimensional images generated using, for example, magnetic resonance imaging (MRI), computed tomography (CT) and positron emission tomography (PET). In some embodiments, the navigation system uses a tracking or localizing system and locates markers attached or fixed to an object, such as an instrument or a patient, and tracks the position of markers. In some embodiments, these tracking systems are optical and magnetic, but also include acoustic systems. In some embodiments, optical systems have a stationary stereo camera pair that observes passive reflective markers or active infrared LEDs attached to the tracked tools. In some embodiments, magnetic systems have a stationary field generator that emits a magnetic field that is sensed by small coils integrated into the tracked tools. In some embodiments, the virtual surgical field comprises a display of one or more diagnostic or planning image(s), for example, x-ray images, computed tomography images, MM images, MRA images, MR spectrometric images, PET images, MRV images, SPECT images, CEMRV images, CT angiographic images, CT myelographic images, MR myelographic images, flair images, two-dimensional fluoroscopic images, three-dimensional fluoroscopic images, two-dimensional ultrasonic images, three-dimensional ultrasonic images, ultrasound microscopy images, laparoscopic ultrasound images, optical images, isotopic images, laser depth maps, line arts, sketches, "cartoon" representations, holographic images, or any combination thereof.

Hand-Held Components

Disclosed herein, in some aspects, is a hand-held component. In some embodiments, the hand-held component is configured for manual manipulation. In some embodiments, the hand-held component is an electro-mechanical device that communicates with a user and is configured to be held by the user's hand(s). In some embodiments, the hand-held component provides haptic feedback based on one or more interactions in the simulated or virtual environment. In some embodiments, the hand-held component provides haptic feedback from interaction between a haptic tool and a haptic target. In some embodiments, a hand-held component allows a user to use a virtual surgical instrument to touch and manipulate virtual objects within the virtual surgical field. The hand-held component may be connected to a processor wirelessly or via a connector, e.g., a USB cable or coaxial cable or other cable. The processor may be a central processing unit ("CPU") located in a laptop computer or desktop computer, or other device whether hand-held or not, and which may display the virtual surgical field on a monitor screen or other display. In some embodiments, the hand-held component comprises an arm, a keyboard, a pointer, a wand, a joystick, a mouse, a roller, a grasper, a handle, or a glove (e.g., a haptic glove). In some embodiments, the hand-held component comprises two arms configured to provide haptic feedback. In some embodiments, before use, the hand-held component is calibrated with a software/computer program disclosed herein.

In some embodiments, the hand-held component is attached or coupled to a base. In some embodiments, the hand-held component is configured to pivot, rotate, translate, and/or otherwise move in relation to the base to which it is attached. In some embodiments, the hand-held component is connected to a base by one or more wires or cables. In some embodiments, the hand-held component is connected to a base by a joint. In some embodiments, the base comprises the processor and/or is in communication with the processor. In some embodiments, the hand-held component comprises a power source or connection such as, for example, a power cable or a battery (single-use or rechargeable). In some embodiments, the hand-held component comprises one or more motors that provide haptic feedback such as, for example, pressure, resistance, vibrations, and other tactile feedback. In some embodiments, the hand-held component is attached to a base and provides one or more degrees of freedom. In some embodiments, the hand-held component provides at least two, at least three, at least four, at least five, at least six, or at least seven degrees of freedom. The hand-held component can provide freedom of motion such as, for example, moving up and down, moving left and right, moving forward and backward, swiveling left and right, tilting forward and backward, and pivoting side to side. In some embodiments, the hand-held device comprises a chain of one or more links connected by joints. In some embodiments, each joint provides one or more degrees of freedom (e.g., moving left and right or rotation). In some embodiments, the chain of links is attached or secured to a base.

In some embodiments, a haptic feedback felt by a user holding the hand-held components comprises pressure, force, velocity, motion, sensation, position, depth, width, surface, layer, contour, density, texture, resistance, direction, hardness, stiffness, softness, contraction, elasticity, flexibility, release, freedom, torque, rotation, contact, collision, any combination thereof, or any degree, magnitude, or duration thereof. In some embodiments, the force corresponds to a gripping of the object of interest with a virtual surgical instrument. In some embodiments, a degree of haptic feedback is determined as a degree of sensation, a degree of rotation, degree of retraction, degree of firmness, degree of freedom (DOF), magnitude, duration of a signal/feedback, or dynamic property of the force and/or torque, or any combination thereof. The haptic interaction forces and/or torques may be repulsive, attractive, frictional, viscous, impulsive, detent, regulatory (for example designed to maintain cutting speeds or feed rates), or any combination thereof. In some embodiments, a haptic feedback comprises a variation of signal in terms of types and degrees/intensities over a duration, for example, feeling a change from a firm density to a softer texture for a certain period of duration, when scorching cartilage white whilst slowly penetrating with an electrocautery or cauterizing pen.

In some embodiments, a type or degree of haptic feedback is connected to a user's particular virtual experience. For example, when a user is cutting through a dense tissue such as bone, the hand-held component generates a resistive force on a hand of the user. In some embodiments, the amount of resistance generated is directly related to the virtual tissue type. Another example, when a user is using a virtual surgical instrument such as a sharp scalpel, the hand-held component generates a realistically varying degree of resistance and difficulty such that the sharp scalpel cleanly cuts skin and muscle, barely marks cortical bone, and cuts cartilage with resistance and difficulty. Another example, when a user is using a virtual surgical instrument such as a sagittal saw, the hand-held component generates a motion that the sagittal saw oscillates and tears skin, a pressure or contact for a certain period of duration from cleanly cutting bone, and a torque and strength of force from cutting cartilage with ripping action.

Users' Experience

A user disclosed herein is a human subject, e.g., a surgeon, a trainee, a clinician, or a student who uses a system, device, object, instrument, software, or method disclosed herein. In some embodiments, the user holds a hand-held component, which interacts with a processor, to control a virtual surgical instrument to perform a realistically simulated surgery. In some embodiments, the processor presents a virtual image on a display and allows the user to touch, manipulate, modify, or otherwise interact with virtual objects within a virtual surgical field. In some embodiments, the display is configured to show movement of the virtual surgical instrument based on motions of the hand-held component and to provide feedback (e.g., haptic feedback) to the user holding the hand-held component depending on the position of the virtual surgical instrument. In some embodiments, the display is head mounted such that the virtual image may be presented on a display screen located on a virtual reality headset, helmet, googles, goggles, eyeglasses, or other headgear. In some embodiments, the system, methods, and software disclosed herein allow the user to perform simulated surgery while in a complete virtual world (e.g., as viewed through the display).

In some embodiments, a user's experience comprises receiving an input generated by a hand-held controller (e.g., user input/manipulation of the hand-held controller), determining a location in space of a virtual surgical tool based on the input (e.g., a virtual tool corresponding to the hand-held controller), and/or determining whether the virtual surgical tool contacts an object with a haptic representation inside the virtual surgical environment, and if it does, next determining the 3D representation at the point of contact, retrieving the haptic properties and susceptibilities associated with the target, and/or transmitting the haptic through the controller. In some embodiments, the 3D representation comprises polygonal vertex data. In some embodiments, the above process comprises determining at least one vertex of the 3D representation associated with the contact, and retrieving haptic information associated with the vertex.

FIG. 1 illustrates an example how a user 101 engages a system disclosed herein with a cross reality (XR) headset 102 (e.g., mixed reality, augmented reality, or mixed reality), a base comprising a processor 103 operatively coupled to a hand-held component 104—two haptic arms that control a virtual object and receive feedback, and a computer 105 comprising a computer program configured to communicate with the processor.

In some embodiments, a virtual surgical field disclosed herein represents one of many surgical fields available from the system, and each surgical field provides a different experience for a user, e.g., a hip replacement surgery, a knee replacement surgery, and a spinal surgery.

Figure 2:
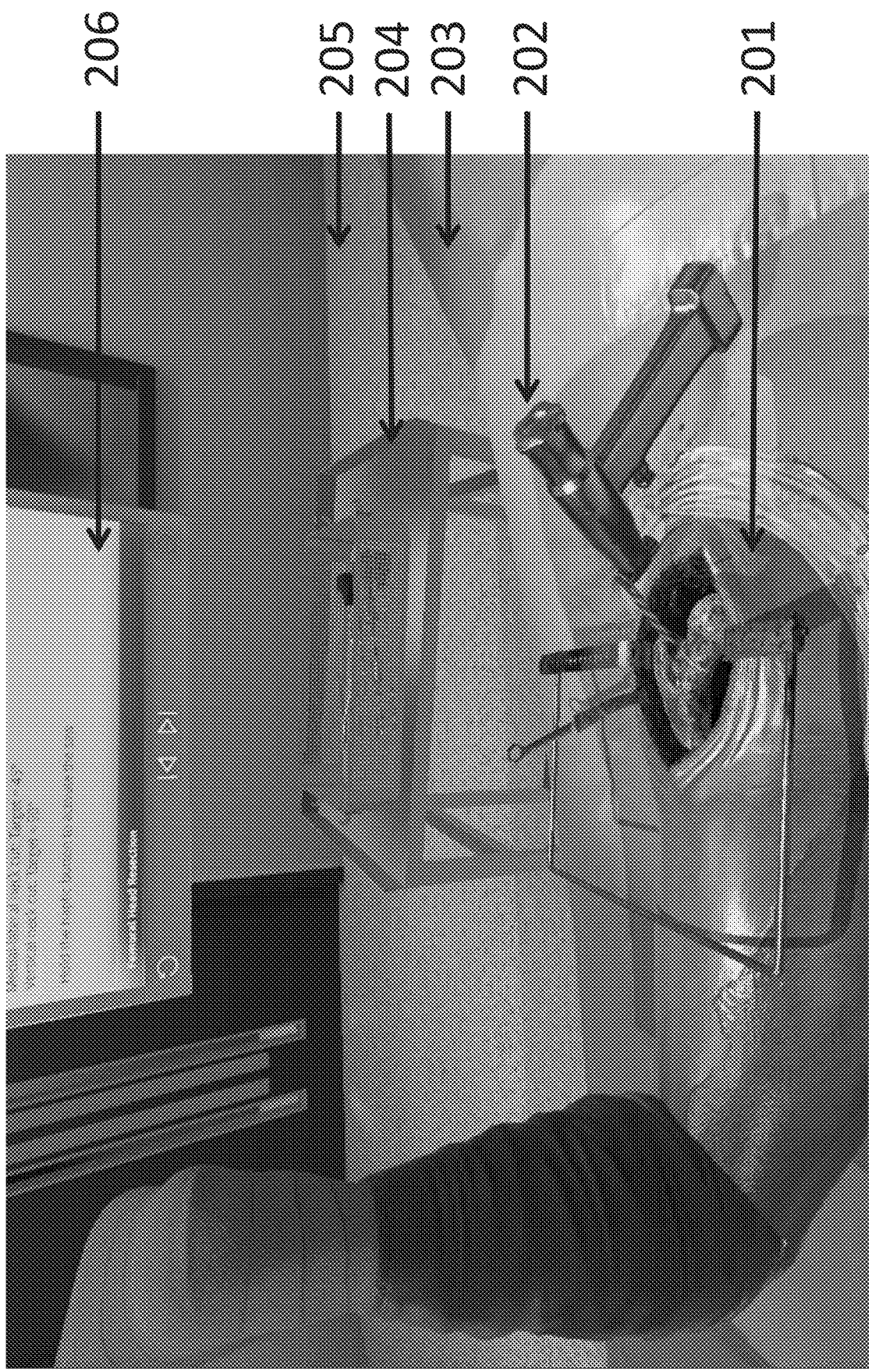
FIG. 2 shows an exemplary virtual operation room for a hip replacement surgery.

FIG. 2 shows an exemplary virtual operation room for a hip replacement surgery. This figure shows part of what a user engaged with the system actually sees, including a virtual object—hip 201, virtual surgical instruments such as a sagittal saw 202, and a virtual surgical field including an operating table 203, a surgical instrument cart 204 with various tools, a floor 205, and a screen 206 from which the user receives instruction to conduct the surgery.

Figure 3:
FIG. 3 shows an exemplary virtual operation room for a knee replacement surgery.

FIG. 3 shows an exemplary virtual operation room for a knee replacement surgery. This figure shows part of what a user engaged with the system actually sees, including a virtual object-knee 301, virtual surgical instruments such as a sagittal saw 302, and a virtual surgical field including an operating table 303, a surgical instrument cart 304 with various tools, a floor 305, and a screen 306 from which the user receives instruction to conduct the surgery.

Figure 4:
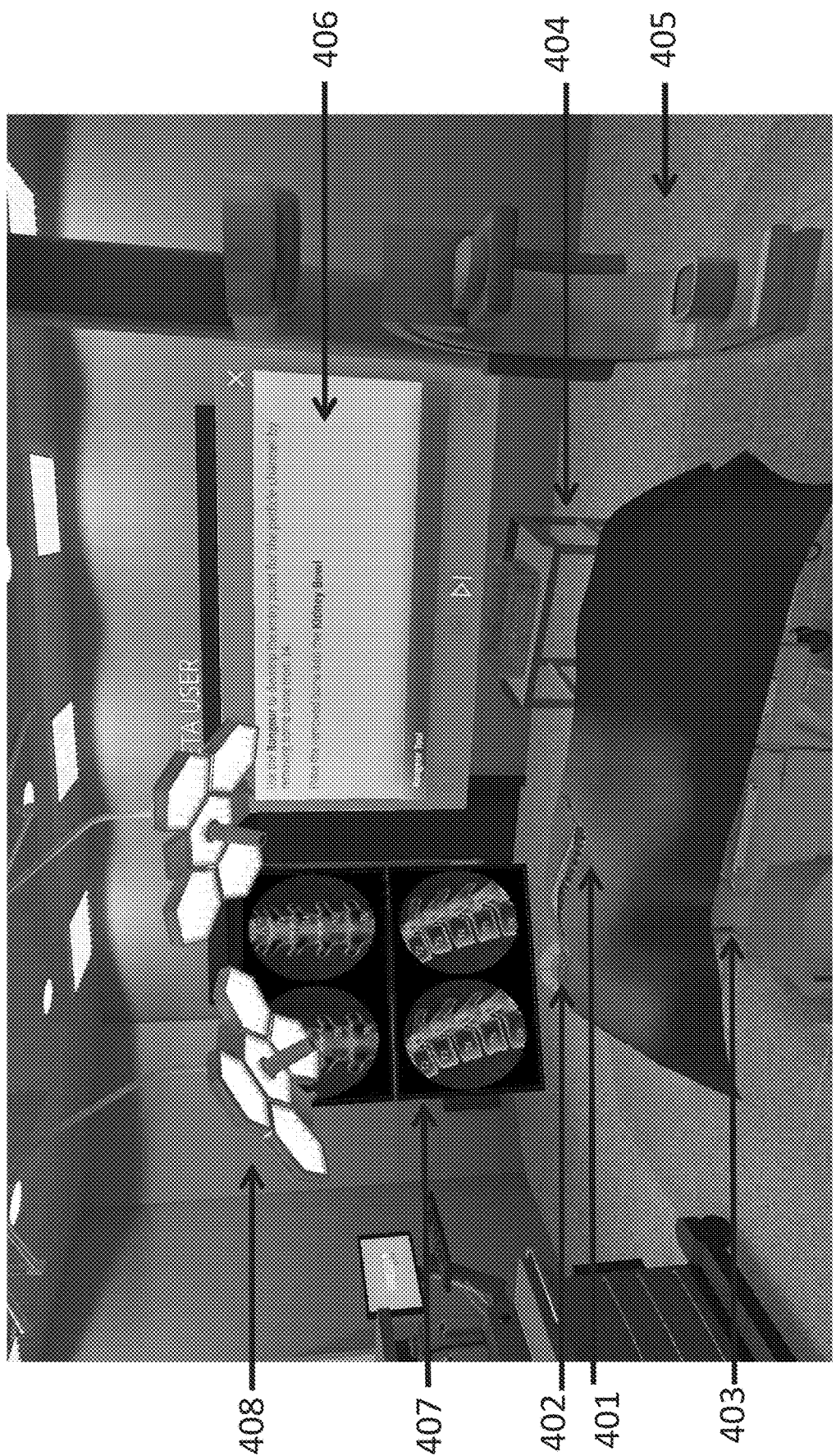
FIG. 4 shows an exemplary virtual operation room for a spinal surgery.

FIG. 4 shows an exemplary virtual operation room for a spinal surgery. This figures shows part of what a user engaged with the system actually sees, including a virtual object-spine 401, virtual surgical instruments such as a retractor 402, a virtual surgical field including an operating table 403, a surgical instrument cart 404 with various tools, a floor 405, a screen 406 from which the user receives instruction to carry out the surgery, x-ray images 407, and surgical lights 408.

Figure 5:
FIG. 5 is a close-up image of the exemplary virtual environment shown in FIG. 4.

FIG. 5 is a close-up image of the exemplary virtual environment shown in FIG. 4, in which a user actually sees the virtual object-spine 501, virtual surgical instruments such as the retractor 502 and a bone screwdriver 503, the surgical instrument cart 504, the floor 505, the screen 506, the x-ray image 507, and a surgical basin container 508.

In some embodiments, a system disclosed herein is capable of providing a user an individual virtual access to a three-dimensional ("3D") environment. Such system may serve as surgical educational or training tools providing a user the ability to practice procedures within a virtual environment using a virtual surgical instrument. In some embodiments, the system can provide a realistic and efficient method to obtain, practice, and refine surgical skills with concomitant instructional feedback and evaluation. In some embodiments, the system allows the user to practice various surgical procedures including creating lines of incision and creating osteotomies in either a 2D or 3D environment. In some embodiments, the system allows the user to "feel" the various densities of bone when preparing osteotomies and to angle the virtual surgical instrument appropriately. For example, the system provides haptic feedback to the user that a virtual surgical instrument such as an electrocautery/cauterizing pen deforms and burns skin brown, scorches bone white without penetrating, and scorches cartilage white whilst slowly penetrating.

In some embodiments, a system disclosed herein is customized to use actual digital imaging data from an actual patient and allow a user to practice an upcoming or proposed surgery prior to the real operation. In some embodiments, digital imaging data is collected from the patient using medical imaging techniques such as X-ray imaging, CAT scan, magnetic resonance imaging (MRI), ultrasonic imaging, endoscopic imaging, tactile imaging, thermographic imaging, photographic imaging, positron emission tomography (PET), single photon emission computed tomography imaging (SPECT), elastographic imaging, photoacoustic imaging, tomographic imaging, echocardiographic imaging, functional near infrared imaging or magnetic particle imaging. For example, digital imaging data of a patient can be produced by taking at least one X-ray or CAT scan image of the area where the surgery is to be performed and then shown in the virtual or simulated environment. Alternatively or additionally, other imaging data may be used such as from an MM or scanned image of a surface model of the surgical site. This data can be used to virtually reconstruct the patient's actual surgical field to be used in the virtual simulation. Such data may include a specific patient's bone structure and formation or bone tissue. In another example, this data may be useful for creating a prosthesis for the patient after the surgery has concluded. The actual digital imaging data may be stored within a database. The database can be a local database (e.g., stored on a local server) or a remote network or cloud database. In some embodiments, the database includes data relating to nonphysical properties or other medical information of a specific patient, such as a patient's medical history, known allergies, and illnesses. In some embodiments, the database may include information pertaining to a patient's treatment plan or procedure. In some embodiments, a processor herein may access the data contained within the database and provide the user access to this data. In some embodiments, a user may access and upload a patient's digital data to the system and use the data to practice a specific patient's planned surgery within a virtual environment.

Enhanced Haptic & Visual Feedback

Disclosed herein, in some aspects, are systems and methods for determining a type and degree of haptic feedback and/or visual feedback that a user experiences when interacting with a cross reality (XR) such as, for example, a virtual, augmented, mixed, or simulated reality. The feedback can be determined using algorithm(s) that allow dynamic computation of feedback for interactions between a hand-held component and a virtual object. An advantage of the present disclosure is the ability to establish a resultant effect of the interaction that is not pre-determined. Instead, the haptic feedback (and/or visual feedback or visual effect) can be determined based on the input and parameters associated with the hand-held component and the virtual object. In some embodiments, the haptic feedback and/or visual feedback is computed using an algorithm based on the input, an affordance value of the instrument represented by the hand-held component (e.g., a virtual surgical instrument), and a susceptibility value of the virtual object.

In some embodiments, a system as described herein comprises a sensor, e.g., a hand-held component, for providing haptic feedback and/or receiving user feedback or input. In some embodiments, the user interacts with a virtual object within the simulation using the physical hand-held component. In some embodiments, the hand-held component is represented in the cross reality (XR) (e.g., virtual, mixed, or simulated reality) as a virtual instrument such as, for example, a surgical instrument or tool. In some embodiments, the haptic and/or visual feedback is associated with an input conveyed through the handheld component. In some embodiments, the input corresponds to an interaction with a virtual object within the simulation.

Without the benefits of the systems and methods disclosed herein, it would be necessary to individually program the interaction between each combination of tool and target in order to create a sufficiently broad simulation, causing an exponential increase in complexity and effort for a linear increase in the number of tools. The systems and methods disclosed herein can create an abstraction layer between a tool and associated affordance and a target and associated susceptibility for a given interaction, which enables us to calculate the effects generated in a systematic and generalizable way. With this method, complexity and effort are proportional to the number of affordances and susceptibilities. The number of these can be smaller than the number of tools and targets by several orders of magnitude.

In some embodiments, the systems and methods described herein provide a limited number of possible affordances that a hand-held component (e.g., a haptic tool) can implement along with a matching number of possible susceptibilities to which a haptic target (e.g., virtual object such as an organ or tissue) can respond. Each affordance and susceptibility is assigned a value (e.g., a number), which are then combined to establish the nature of the interaction between the hand-held component and the haptic target(s). In some embodiments, the type of interaction between the haptic tool and the haptic target will correspond to a type of affordance and susceptibility. Non-limiting examples of interaction types include cutting/sharpness (e.g., whether a tool can cut a target), cauterization (e.g., how a tool can cauterize the target tissue or organ), sawing (e.g., how a sawing tool can oscillate to cut through bone), and penetration (e.g., how a needle, cannula or other pointed instrument can be inserted into tissue).

As an example, a haptic tool is assigned a sharpness/cutting affordance and a haptic target is assigned a sharpness/cutting susceptibility, and these values can be combined algorithmically and translated into actions and effects (e.g., haptic and visual feedback) in the simulation for a "cutting" interaction type. In this example, if the haptic tool has an affordance value for cutting of 50, when combined with a haptic target with a cutting susceptibility of 30, the resultant effect will be dependent upon the algorithmic combination of the 50 affordance value and 30 susceptibility value and the force with which the haptic tool is used (e.g., the input of the user). If the affordance and susceptibility values and the input force are algorithmically determined to indicate a successful cutting interaction, then the appropriate haptic feedback and/or visual feedback is provided. The haptic feedback can comprise high resistance to the cutting motion/input when the algorithm determines a weak successful cut, for example, when the tool corresponds to a virtual surgical instrument like a scalpel that is being used to cut a hard and dense tissue such as bone. In some embodiments, the haptic feedback comprises moderate resistance to the cutting motion/input when the algorithm determines a moderately successful cut, for example, when the tool corresponds to a virtual surgical instrument like a scalpel that is being used to cut a tough tissue such as cartilage. In some embodiments, the haptic feedback comprises low resistance to the cutting motion or input when the algorithm determines a strong successful cut, for example, when the tool corresponds to a virtual scalpel being used to cut virtual skin or muscle tissue. This feedback may vary depending on the input such as the amount of force conveyed through the tool. For example, a large force may be needed to achieve the minor cutting of bone using a scalpel, whereas a small force may result in no effect.

In some embodiments, the visual feedback is algorithmically determined using the affordance value, susceptibility value, and input. Accordingly, the visual feedback can comprise the visual effect of the virtual tissue or organ being cut in a manner consistent with the haptic feedback. For example, the visual effect can show the bone being barely cut by the scalpel, the cartilage being moderately cut by the scalpel, or the skin or muscle tissue being easily cut by the scalpel. Conversely, if the tool and target have no matching affordances and susceptibilities according to the algorithmic calculation, then the haptic tool has no effect on the target. This lack of effect can comprise visual feedback and/or haptic feedback. The visual feedback for no effect from the cutting interaction may comprise showing the tool not successfully cutting the target within the simulation. The haptic feedback for no effect may comprise high resistance to the user input or motion (e.g., pushing back or holding firm against the user attempts to "cut into" the virtual object). In another example, the user is simulating the cutting of virtual skin with a virtual scalpel. A successful cut will generate a visual feedback that reflects the affordance value of the scalpel, susceptibility value of the skin, and input value of the force and movement applied by the user. If the user applies appropriate force, the visual feedback generated may show the cutting of the virtual skin. If the user applies excessive force, the visual feedback generated may show the cutting of the virtual skin, the cutting of the virtual subcutaneous tissue, and the cutting of a virtual muscle.

The visual feedback can comprise a visual effect on the virtual object. Non-limiting examples of the visual effect include deformation, a burning, a color change or discoloration, a clean cut, a minor cut, tearing or ripping, grinding, lacerating, and freezing. In some embodiments, the visual feedback is associated with a virtual object and virtual tool. For example, the application of a virtual tool that generates heat (e.g., a cauterization pen) may cause one visual effect on virtual skin and another visual effect on virtual bone or virtual cartilage. In some embodiments, the visual feedback is associated with the users input. For example, a user inputs an imperfect surgical cut due to shaky hand movements and the visual effect generated displays a jagged or incomplete cut.

Figure 7A:
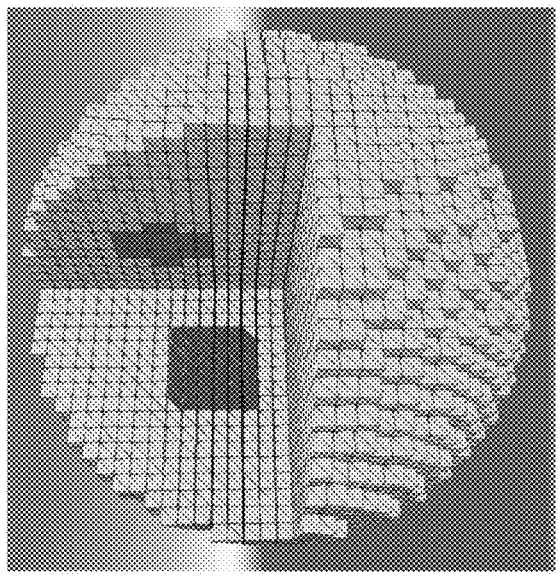
FIG. 7A shows a voxel data representation containing tissue type information indicated by the different colors.
Figure 7B:
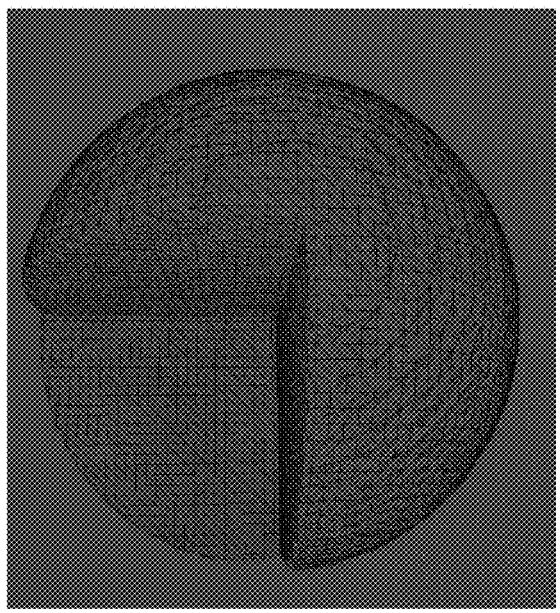
FIG. 7B shows a mesh generated from the same voxel data represented in FIG. 7A.
Figure 7C:
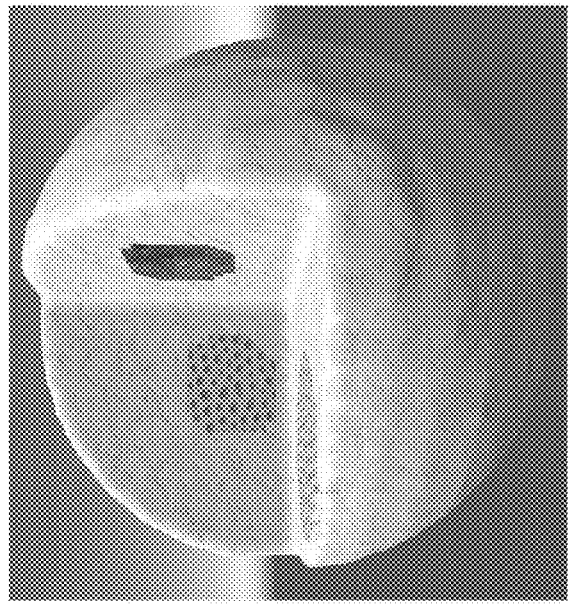
FIG. 7C shows a render of the virtual object with different tissue types.

FIG. 7A shows a voxel data representation containing tissue type information indicated by the different colors. As used herein, a voxel is well-known in the field as representing a value on a grid in three-dimensional space. The individual voxels are shown as cubes that make up the roughly spherical three-dimensional object. FIG. 7B shows a mesh generated from the same voxel data represented in FIG. 7A. The three-dimensional mesh provides the shape of the three-dimensional object that is rendered in the visual render pipeline. In some embodiments, the voxel data is used to generate or render a three-dimensional mesh. FIG. 7C shows a single object with multiple textures that can provide differential haptic and/or visual feedback in response to interaction types and input forces applied by a user. As an example, when a user is chipping away at the outer surface of the bone (cortical bone) to expose the interior bone (trabecular bone), the texture or material the user's haptic tool comes into contact with in the simulation may change. Accordingly, the algorithmic calculation that determines the haptic and/or visual feedback resulting from this interaction can change as the corresponding susceptibility value changes from one tissue type to the next.

Haptic feedback using any of the cross reality (e.g., mixed, augmented, or virtual) environments or simulations disclosed herein can be calculated using affordance values of the tool and susceptibility values of the object being acted upon by the tool. In some embodiments, the values are normalized to a range or scale, for example, between 0 and 1. This allows for the efficient calculation of haptic feedback and/or visual effects based on affordance and susceptibility values. In some embodiments, a tool has a first set of affordance value(s) when powered off, and a second set of affordance value(s) when powered on. For example, a surgical drill that is switched off may have the following affordance values: BluntPressure=0.09; SharpPressure=0.1; CuttingBlade=0.0; CuttingSaw=0.0; Drilling=0.0. Alternatively, when the surgical drill is powered on, it may have different affordance values: BluntPressure=0.00; SharpPressure=0.1; CuttingBlade=0.0; CuttingSaw=0.0; Drilling=0.75. Thus, the affordance value increases from 0.0 to 0.75 when the drill is powered on, which can result in a substantial difference in the resulting haptic and/or visual feedback when the drill is contacted or applied against an object (e.g., virtual bone).

In some embodiments, the affordance and susceptibility values are used to determine a damage multiplier. This damage multiplier can be used as a multiplier to determine the amount by which a user's tool pressure damages the object (which can result in visual feedback) and/or determine the amount of force the object applies to the tool (e.g., haptic feedback). For example, a low damage multiplier may mean a user has to apply a large degree of pressure (e.g., pressing the tool against the object) in order to cause damage (e.g., successfully drilling a hole in a bone), which in turn may provide corresponding haptic feedback (e.g., tool provides resistance to the user's application of pressure). Alternatively, a high damage multiplier may mean a user can successfully drill through the bone by applying a relatively lower degree of pressure as compared to when the damage multiplier has a lower value. Various formulas can be used to calculate the damage multiplier. As a non-limiting example, Damage Multiplier=(Drill BluntPressure Affordance*Bone BluntPressure Susceptibility)+(Drill SharpPressure Affordance*Bone SharpPressure Susceptibility). The damage multiplier can be used in combination with an object's damage threshold to determine the units of pressure a user needs to apply in order to successfully achieve the desired effect on the object. For example, the damage threshold can be divided by the damage multiplier to generate a number of units of pressure. In some embodiments, user input comprises an amount of units of pressure provided through the tool. In some embodiments, the amount of units of pressure is delineated by a lower bound and an upper bound such as in a range. In some embodiments, having a number of pressure units that is above an upper bound or threshold effectively indicates that a user cannot achieve the desired effect on the object (e.g., drilling into bone, cutting through muscle, etc.). For example, in the case of an unpowered drill, the damage multiplier may be determined to be 0.005. If the bone's damage threshold is 0.1, then dividing the damage threshold by the damage multiplier results in 20 units of pressure required to successfully drill into the bone. The upper threshold may be 5 units of pressure, in which case the 20 units of pressure means the user will be unable to drill into the bone with an unpowered drill. Likewise, if the damage multiplier comes out to be 0.5, then the above formula would indicate 0.2 units of pressure is required. The 0.2 units of pressure may correspond to a relatively low amount of force that the user would need to apply in order to successfully drill into the bone.

In some embodiments, a unit of pressure is pegged to a certain amount of force (e.g., a specific number of Newtons).

Systems for Determining Haptic and Visual Feedback

In some embodiments, a system as described herein is configured to determine a type and degree of haptic feedback that a user experiences and/or visual feedback. In some embodiments, a system as described herein comprises a sensor, e.g., a hand-held component, for providing haptic feedback and/or receiving feedback or input from a user. In some embodiments, the system comprises a display for showing the visual feedback.

In some embodiments, a system as described herein comprises a network element for communicating with a server. In some embodiments, the server is part of the system. In some embodiments, the system is configured to upload to and/or download data from the server. In some embodiments, the server is configured to store sensor data, haptic feedback type(s) and degree(s), and/or other information for the subject. In some embodiments, the server is configured to store historical data for the subject. In some embodiments, the server is configured to backup data from the system or apparatus. In some embodiments, a system as described herein is configured to perform any of the methods described herein.

In some embodiments, a system as described herein comprises a processor; a hand-held component operatively coupled to the processor; and a non-transitory computer readable storage medium encoded with a computer program configured to communicate with the processor. In some embodiments, a processor disclosed herein is part of or linked to a computer and includes or is operatively coupled to a graphics card, a monitor, and/or a cross reality (XR) headset. In some embodiments, the computer program that causes the processor to: (i) display a virtual object as part of a virtual surgical field, wherein the virtual object is associated with a susceptibility value; (ii) display a movement of a virtual surgical instrument within the virtual surgical field based on an input from the hand-held component when a user moves the hand-held component, wherein the virtual surgical instrument is associated with an affordance value; (iii) determine a haptic value based on the susceptibility value, the input, and the affordance value when the virtual surgical instrument is displayed in an interaction with the virtual object within the virtual surgical field; and (iv) transmit the haptic feedback to the hand-held component wherein a quantity of the haptic feedback that is transmitted is determined based on the haptic value. In some embodiments, the computer program further causes the processor to display a movement of the virtual surgical instrument in the surgical field in the same direction as a movement of the hand-held component based on the input. In some embodiments, the interaction comprises moving the object of interest with the virtual surgical instrument and the computer program further causes the processor to display a movement of the object of interest, including its associated texture(s). In some embodiments, the interaction comprises cutting the object of interest and the computer program further causes the processor to display an interior surface of the virtual object that is different than the exterior surface. In some embodiments, the computer program further causes the processor to simultaneously display the interior and exterior surfaces of the object. In some embodiments, the interior surface and the exterior surface have different textures. In some embodiments, the interaction comprises applying a force to the virtual object with the virtual surgical instrument and the computer program further causes the processor to display a response of the virtual object to the force. In some embodiments, the interaction is displayed seamlessly during the period that the interaction is displayed. In some embodiments, the object is associated with a plurality of susceptibility values. In some embodiments, the plurality of susceptibility values correspond to different susceptibility types such as, for example, susceptibility to blunt pressure, sharp pressure, cutting blade, cutting saw, drilling, and other types of tool-to-object interactions. In some embodiments, the susceptibility types include drilling, sawing, penetrating, cutting, squeezing or clamping, pressing/pushing, or any combination thereof. In some embodiments, the susceptibility values correspond to different tissue types. As an example, a virtual leg object may have various susceptibility values for its skin, muscle, bone, and cartilage components.

In some embodiments, the system or apparatus is configured to encrypt data. In some embodiments, data on the server is encrypted. In some embodiments, the system or apparatus comprises a data storage unit or memory for storing data. In some embodiments, data encryption is carried out using Advanced Encryption Standard (AES). In some embodiments, data encryption is carried out using 128-bit, 192-bit, or 256-bit AES encryption. In some embodiments, data encryption comprises full-disk encryption of the data storage unit (e.g., encrypting the entire hard drive on a server or apparatus). In some embodiments, data encryption comprises virtual disk encryption (e.g., encrypting a folder containing sensor data files for a subject). In some embodiments, data encryption comprises file encryption (e.g., encrypting sensor data files for a subject). In some embodiments, data that is transmitted or otherwise communicated between the system or apparatus and other devices or servers is encrypted during transit. In some embodiments, wireless communications between the system or apparatus and other devices or servers is encrypted. As an example, an apparatus that is integrated with a haptic tool sends and/or receives data wirelessly using an encrypted data channel. In some embodiments, data in transit is encrypted using a Secure Sockets Layer (SSL). In some embodiments, access to data stored on the system or apparatus as described herein requires user authentication. In some embodiments, access to data stored on the server as described herein requires user authentication.

An apparatus as described herein comprises a digital processing device that includes one or more hardware central processing units (CPUs) or general purpose graphics processing units (GPGPUs) that carry out the device's functions. The digital processing device further comprises an operating system configured to perform executable instructions. The digital processing device is optionally connected to a computer network. The digital processing device is optionally connected to the Internet such that it accesses the World Wide Web. The digital processing device is optionally connected to a cloud computing infrastructure. Suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein.

Typically, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing.

A digital processing device as described herein either includes or is operatively coupled to a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

A system or method as described herein can be used to generate, determine, and/or deliver a degree of haptic feedback which may then be used to determine whether a subject value falls within or outside of a threshold value. In addition, in some embodiments, a system or method as described herein generates a database as containing or comprising one or more haptic feedback degrees. In some embodiments, a database herein provides a relative risk of presence/absence of a status (outcome) associated with haptic feedback that fall either within or outside of a threshold value.

Some embodiments of the systems described herein are computer based systems. These embodiments include a CPU including a processor and memory which may be in the form of a non-transitory computer-readable storage medium. These system embodiments further include software that is typically stored in memory (such as in the form of a non-transitory computer-readable storage medium) where the software is configured to cause the processor to carry out a function. Software embodiments incorporated into the systems described herein contain one or more modules.

In various embodiments, an apparatus comprises a computing device or component such as a digital processing device. In some of the embodiments described herein, a digital processing device includes a display to send visual information to a user. Non-limiting examples of displays suitable for use with the systems and methods described herein include a liquid crystal display (LCD), a thin film transistor liquid crystal display (TFT-LCD), an organic light emitting diode (OLED) display, an OLED display, an active-matrix OLED (AMOLED) display, or a plasma display.

A digital processing device, in some of the embodiments described herein includes an input device to receive information from a user. Non-limiting examples of input devices suitable for use with the systems and methods described herein include a keyboard, a mouse, trackball, track pad, or stylus. In some embodiments, the input device is a touch screen or a multi-touch screen.

The systems and methods described herein typically include one or more non-transitory computer-readable storage media encoded with a program including instructions executable by the operating system of an optionally networked digital processing device. In some embodiments of the systems and methods described herein, the non-transitory storage medium is a component of a digital processing device that is a component of a system or is utilized in a method. In still further embodiments, a computer-readable storage medium is optionally removable from a digital processing device. In some embodiments, a computer-readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Typically the systems and methods described herein include at least one computer program, or use of the same. A computer program includes a sequence of instructions, executable in the digital processing device's CPU, written to perform a specified task. Computer-readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages. The functionality of the computer-readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Typically, the systems and methods described herein include and/or utilize one or more databases. In view of the disclosure provided herein, those of skill in the art will recognize that many databases are suitable for storage and retrieval of baseline datasets, files, file systems, objects, systems of objects, as well as data structures and other types of information described herein. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

FIG. 6 shows exemplary embodiments of a system as described herein comprising an apparatus such as a digital processing device 601. The digital processing device 601 includes a software application configured to determine a type and degree of haptic feedback to a user. The digital processing device 601 may include a central processing unit (CPU, also "processor" and "computer processor" herein) 605, which can be a single core or multi-core processor, or a plurality of processors for parallel processing. The digital processing device 601 also includes either memory or a memory location 610 (e.g., random-access memory, read-only memory, flash memory), electronic storage unit 615 (e.g., hard disk), communication interface 620 (e.g., network adapter, network interface) for communicating with one or more other systems, and peripheral devices, such as cache. The peripheral devices can include storage device(s) or storage medium 665 which communicate with the rest of the device via a storage interface 670. The memory 610, storage unit 615, interface 620 and peripheral devices are configured to communicate with the CPU 605 through a communication bus 625, such as a motherboard. The digital processing device 601 can be operatively coupled to a computer network ("network") 630 with the aid of the communication interface 620. The network 630 can comprise the Internet. The network 630 can be a telecommunication and/or data network.

The digital processing device 601 includes input device(s) 645 to receive information from a user, the input device(s) in communication with other elements of the device via an input interface 650. The digital processing device 601 can include output device(s) 655 that communicates to other elements of the device via an output interface 660.

The CPU 605 is configured to execute machine-readable instructions embodied in a software application or module. The instructions may be stored in a memory location, such as the memory 610. The memory 610 may include various components (e.g., machine readable media) including, but not limited to, a random access memory component (e.g., RAM) (e.g., a static RAM "SRAM", a dynamic RAM "DRAM, etc.), or a read-only component (e.g., ROM). The memory 610 can also include a basic input/output system (BIOS), including basic routines that help to transfer information between elements within the digital processing device, such as during device start-up, may be stored in the memory 610.

The storage unit 615 can be configured to store files, such as health or risk parameter data, e.g., individual health or risk parameter values, health or risk parameter value maps, and value groups. The storage unit 615 can also be used to store operating system, application programs, and the like. Optionally, storage unit 615 may be removably interfaced with the digital processing device (e.g., via an external port connector (not shown)) and/or via a storage unit interface. Software may reside, completely or partially, within a computer-readable storage medium within or outside of the storage unit 615. In another example, software may reside, completely or partially, within processor(s) 605.

Information and data can be displayed to a user through a display 635. The display is connected to the bus 625 via an interface 640, and transport of data between the display other elements of the device 601 can be controlled via the interface 640.

Methods as described herein can be implemented by way of machine (e.g., computer processor) executable code stored on an electronic storage location of the digital processing device 601, such as, for example, on the memory 610 or electronic storage unit 615. The machine executable or machine readable code can be provided in the form of a software application or software module. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

In some embodiments, a remote device 602 is configured to communicate with the digital processing device 601, and may comprise any mobile computing device, non-limiting examples of which include a tablet computer, laptop computer, smartphone, or smartwatch. For example, in some embodiments, the remote device 602 is a smartphone of the user that is configured to receive information from the digital processing device 601 of the apparatus or system described herein in which the information can include a summary, sensor data, types and degrees of haptic feedback, or other data. In some embodiments, the remote device 602 is a server on the network configured to send and/or receive data from the apparatus or system described herein.

Some embodiments of the systems and methods described herein are configured to generate a database comprising one or more types and degrees of haptic feedback and/or threshold value. A database, as described herein, is configured to function as a user's learning tool or a lookup table to evaluate a user's performance, e.g., after a simulated surgery is completed. In some embodiments, types and degrees of haptic feedback are presented in a database so that a user is able to identify whether a parameter of a specific subject falls within or outside of a threshold value. In some embodiments, the database is stored on a server on the network, or stored locally with data backup provided by a server. In some embodiments the database is stored locally on the apparatus or the system.

Certain Definitions

As used herein, the singular forms "a", "an" and "the" include plural references unless the context clearly dictates otherwise. For example, the term "a sample" includes a plurality of samples, including mixtures thereof. Any reference to "or" herein is intended to encompass "and/or" unless otherwise stated.

As used herein, the term "about" a number refers to that number plus or minus 10% of that number. The term "about" a range refers to that range minus 10% of its lowest value and plus 10% of its greatest value. The lower and upper bounds for "about" a number are rounded up. For example, a frame-rate of about 105 indicates a frame-rate range of 95 to 116 (105−10.5 for 94.5 which is rounded up to 95; and 115+10.5 for 115.5 which is rounded up to 116).

As used herein, the phrases "at least one of a, b, c, and d" and "at least one of a, b, c, or d" refer to a, b, c, or d, and any and all combinations comprising two or more than two of a, b, c, and d.

As used herein, the term "XR" or "cross reality" refers to an augmented, virtual, and/or mixed reality environment and can encompass a wide range of hardware and software, including sensors, interfaces, software applications, and other tools useful for generating this reality. Wherever any one category of "XR" or "cross reality" is referenced herein (e.g., "augmented reality," "virtual reality," or "mixed reality"), the other forms of cross reality are also denoted. Thus, a reference to an augmented reality system would also indicate a virtual reality system and a mixed reality system as well as the broader category of a cross reality system.

As used herein, "virtual reality" refers to an interactive experience within a computer-simulated environment that engages one or more senses.

As used herein, "mixed reality" or "hybrid reality" refers to an interactive experience that merges both the real world environment and a virtual environment to produce a hybrid environment that combines sensory modalities from both the real and virtual such that physical and digital objects can coexist and optionally interact.

As used herein, "augmented reality" refers to an interactive experience with the real world environment in which physical or otherwise real objects present in the real world environment are "augmented" with computer-generated sensory information such as visual, auditory, or haptic.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1—Haptic Feedback in Simulated Surgical Cutting

A mixed reality simulation system is provided that includes a set of VR goggles, a haptic tool operatively connected to the system, and a computing system configured to determine haptic and visual feedback based on interactions within the simulation. A user wears the VR goggles and manually manipulates the haptic tool. The simulation is a surgical simulation in which the user sees an operating room with a virtual leg positioned on an operating table (see, e.g., FIG. 2). The haptic tool corresponds to a virtual instrument that is a scalpel. The user moves the haptic tool, which causes a corresponding movement of the virtual scalpel within the surgical simulation as displayed through the VR goggles. The haptic tool moves with minimal resistance as the virtual scalpel moves without contacting any other virtual object. Then the user manipulates the haptic tool to bring the virtual scalpel into contact with the outermost skin layer of the virtual leg. The user then uses the haptic tool to "cut" into the skin. The cutting affordance value of the scalpel and the susceptibility value of the skin are such that even a low force applied by the user through the haptic tool causes the skin to be cut open within the simulation. Accordingly, as the user manipulates the haptic tool to cause the virtual scalpel to slide along the surface of the skin, the visual effect on the skin is that it is cut open to reveal the underlying muscle and connective tissue. The haptic feedback is minimal resistance to the haptic tool's motion.

The user then presses the haptic tool to cause the scalpel to cut into the muscle. As the scalpel cuts into the muscle, the user encounters increased resistance due to the interaction between the scalpel's affordance value and the susceptibility value of the muscle tissue. Accordingly, the user applies increased pressure through the haptic tool to cut through the muscle. However, upon encountering the bone, the scalpel meets very high resistance due to the bone's susceptibility value. Here, the user applies a higher force through the haptic tool, but only manages to scratch the bone. Finally, the user attempts to cut through cartilage around the hip joint with the scalpel. The algorithm determining the haptic feedback results in an increased resistance relative to the muscle but lower resistance than bone. The user is able to apply moderate pressure through the haptic tool in order to successfully cut through the virtual cartilage. The visual feedback is determined using the same mechanism as the haptic feedback. Specifically, the algorithm determining haptic feedback also generates an output corresponding to the visual feedback. Thus, the combined haptic and visual feedback provides a consistent feedback to the user's input.

Example 2—Haptic Feedback in Simulated Electrocautery

A mixed reality simulation system is provided that includes a set of VR goggles, a haptic tool operatively connected to the system, and a computing system configured to determine haptic and visual feedback based on interactions within the simulation. A user wears the VR goggles and manually manipulates the haptic tool. The haptic tool corresponds to an electrocautery instrument or cauterizing pen. The visual feedback generated in response to the implementation of the virtual tool is determined by the identity of the virtual object and tool, and the user's input. The user inputs the required movements to "touch" the virtual cauterizing pen with an exterior skin virtual object. In response, the exterior skin changes color from white to brown. The extent of the color change is determined by the length of the contact between the virtual tool and virtual object. In an interaction with a virtual bone, the user generates scorch marks on the virtual bone using the virtual cauterization pen. When the user applies the virtual cauterization pen to virtual cartilage or virtual fat, the cartilage is slowly penetrated by the virtual cauterization, the penetration time being related to the force the user exerts and the susceptibility value of the virtual cartilage or fat and affordance value of the cauterization pen.

Example 3—Haptic Feedback in Simulated Amputation

A mixed reality simulation system is provided that includes a set of VR goggles, a haptic tool operatively connected to the system, and a computing system configured to determine haptic and visual feedback based on interactions within the simulation. A user wears the VR goggles and manually manipulates the haptic tool. The simulation is a surgical simulation in which the user sees an operating room with a virtual leg positioned on an operating table. The haptic tool corresponds to a virtual instrument that is a sagittal saw. The user moves the haptic tool, which causes a corresponding movement of the virtual saw within the surgical simulation as displayed through the VR goggles. The user is able to observe the visual effect of the saw's motion, and feel the oscillation of the virtual electric saw in the haptic tool. The haptic tool moves with minimal resistance as the virtual saw moves without contacting any other virtual object. The user manipulates the haptic tool to bring the virtual saw into contact with bone. The cutting affordance value of the saw and the susceptibility value of the bone are such that a low force applied by the user through the haptic tool results in the bone being cut slowly. Accordingly, as the user manipulates the haptic tool to cause the virtual saw to move into the bone, the visual effect on the bone is that it is cut open to reveal the underlying bone marrow. When the user increases the force applied to the haptic tool, the virtual saw moves through the bone more quickly and the haptic tool provides increased resistance. Upon the completion of the cut, the visual effect displays a clean cut to the bone.

In another setting, the sagittal saw is used to cut skin or cartilage. The application of the virtual oscillating saw to the virtual skin or virtual cartilage produces a visual effect of tearing the skin or cartilage. This is in contrast to the visual effect generated by the application of a virtual scalpel to virtual skin or virtual cartilage, which results in a smooth cut.

Example 4—Haptic and Visual Feedback in Simulated Surgery

A mixed reality simulation system is provided that includes a set of VR goggles, a haptic tool operatively connected to the system, and a computing system configured to determine haptic and visual feedback based on interactions within the simulation. A user wears the VR goggles and manually manipulates the haptic tool. The simulation is a surgical simulation in which the user sees an operating room with a patient positioned on an operating table. The surgical simulation is configured to simulate removal of a foreign object from the patient's body. The haptic tool corresponds to a virtual instrument that is a scalpel. The user moves the haptic tool, which causes a corresponding movement of the virtual scalpel within the surgical simulation as displayed through the VR goggles. The user presses the virtual scalpel against the skin of the patient.

First, the tool's affordances are checked. In this case, the scalpel affordances are: [BluntPressure=0.00; SharpPressure=0.25; CuttingBlade=1.0; CuttingSaw=0.0; Drill=0.0]

Next, the tool's affordances are cross referenced with the skin's susceptibility: [BluntPressure=0.0; SharpPressure=1.0; CuttingBlade=1.0; CuttingSaw=0.1; Drill=0.75; Damage threshold 0.1]

Ignoring zero values, the following value would be calculated:

Damage Multiplier=(SharpPressure affordance*SharpPressure susceptibility)+(CuttingBlade affordance*CuttingBlade susceptibility)

With the actual numbers entered, the formula produces: Damage Multiplier=(1.0*1.0)+(0.25*1.0)=1.25

This 1.25 value is then used as a multiplier to determine how much the user's tool pressure damages the voxel and to inversely determine how much force the voxel applies to the user's tool.

With a multiplier of 1.25, it can be seen that the user would have to apply 0.08 units of pressure to reach the Skin's damage threshold of 0.1. Below this value, the effective force is zero.

Should the user apply pressure and movement greatly in excess of that required then the applied damage can be capped to a maximum value per second.

Thus, it can be seen that skin is highly susceptible to damage by the scalpel. VFX and haptic feedback can be generated accordingly.

A feedback force of 0.08 is very slight, meaning that the user would feel very little resistance when slicing through skin. For example, in the case that the user cuts through the skin down to bone, the scalpel's affordances remain the same, but the susceptibility of the tissues is quite different.

Bone susceptibility [BluntPressure=0.0; SharpPressure=0.05; CuttingBlade=0.0; CuttingSaw=1.0; Drill=1.0; Damage threshold 0.1]

The calculation is now as follows.

Damage Multiplier=(SharpPressure affordance*SharpPressure susceptibility)

Damage Multiplier=(0.25*0.05)=0.0125

To reach the bone's Damage Threshold of 0.1, the user now has to apply (0.1/0.0125)=8 units of pressure. Accordingly, while the scalpel is capable of being used to damage bone, considerable force would be required. The required amount of force may be determined to be sufficient to damage or break the virtual tool within the simulation.

Example 5—Haptic Feedback in Simulated Femoral Head Removal During Hip Replacement Surgery A mixed reality simulation system is provided that includes a set of VR goggles, a haptic tool operatively connected to the system, and a computing system configured to determine haptic and visual feedback based on interactions within the simulation. A user wears the VR goggles and manually manipulates the haptic tool. The simulation is a surgical simulation in which the user sees an operating room with a virtual patient positioned on an operating table (see, e.g., FIG. 2). The haptic tool corresponds to a virtual instrument that is a Sagittal Saw. The user moves the haptic tool, which causes a corresponding movement of the virtual Saggital Saw within the surgical simulation as displayed through the VR goggles. The haptic tool moves with minimal resistance as the virtual saw moves without contacting any other virtual object. The user manipulates the haptic tool to bring the virtual saw into contact with femoral head of the femur bone. The sawing affordance value of the saw and the susceptibility value of the bone are such that a moderate force applied by the user through the haptic tool results in the bone being sawed into by the virtual saw. Accordingly, as the user manipulates the haptic tool to cause the virtual saw to saw into the bone, the visual effect on the bone is that the virtual saw gradually penetrates into the bone to slice off the top of the bone. When the user increases the force applied to the haptic tool, the virtual saw saws into the bone more quickly and the haptic tool provides increased resistance. Upon the completion of the sawing, the user pulls back the haptic tool to leave a visual effect showing the interior texture of the two pieces of bone that have now been sawed apart.

Example 6—Haptic Feedback in Simulated Drilling During Total Knee Arthroplasty

A mixed reality simulation system is provided that includes a set of VR goggles, a haptic tool operatively connected to the system, and a computing system configured to determine haptic and visual feedback based on interactions within the simulation. A user wears the VR goggles and manually manipulates the haptic tool. The simulation is a surgical simulation in which the user sees an operating room with a virtual patient positioned on an operating table (see, e.g., FIG. 2). The haptic tool corresponds to a virtual instrument that is a surgical drill. The user moves the haptic tool, which causes a corresponding movement of the virtual drill within the surgical simulation as displayed through the VR goggles. The user is able to observe the visual effect of the drill's motion, and feel the spinning of the virtual drill bit in the haptic tool. The haptic tool moves with minimal resistance as the virtual drill moves without contacting any other virtual object. The user manipulates the haptic tool to bring the virtual drill into contact with bone. The drilling affordance value of the drill and the susceptibility value of the bone are such that a low force applied by the user through the haptic tool results in the bone being drilled into by the virtual drill. Accordingly, as the user manipulates the haptic tool to cause the virtual drill to drill into the bone, the visual effect on the bone is that the virtual drill penetrates into the bone to create a hole. When the user increases the force applied to the haptic tool, the virtual drill moves into the bone more quickly and the haptic tool provides increased resistance. Upon the completion of the drilling, the user pulls back the haptic tool, and the virtual drill exits the bone to leave a visual effect showing a hole drilled into the bone.

Example 7—Haptic Feedback Calculations

Haptic feedback using any of the cross reality (e.g., mixed, augmented, or virtual) environments or simulations disclosed herein can be calculated using affordance values of the tool and susceptibility values of the object being acted upon by the tool.

As an example, a tool such as a drill that is switched off, when pressed against bone would cause the following calculations to be performed:

(1) Determine the tool's affordances. In this case, the unpowered drill affordances are: [BluntPressure=0.09; SharpPressure=0.1; CuttingBlade=0.0; CuttingSaw=0.0; Drilling=0.0].

(2) Next, the drill's affordances are cross-referenced against the bone's susceptibility, which have the following values: [BluntPressure=0.0; SharpPressure=0.05; CuttingBlade=0.0; CuttingSaw=1.0; Drilling=1.0]

(3) Assuming the bone is contacted by the tool at a bone voxel that has a Damage Threshold of 0.1, the following calculation can be performed:

Damage Multiplier=(Drill BluntPressure Affordance*Bone BluntPressure Susceptibility)+(Drill SharpPressure Affordance*Bone SharpPressure Susceptibility)

Accordingly, the Damage Multiplier=(0.09*0.0)+(0.1*0.05)=0.005

(4) This Damage Multiplier value (0.005) is then used as a multiplier to determine how much the user's tool pressure damages the voxel and to inversely determine how much force the voxel applies to the user's tool.

With a multiplier of 0.005, it can be seen that the user would have to apply 20 units of pressure to reach the bone's damage threshold of 0.1. Below this value, the effective force is zero.

Thus, in this example, bone is nigh impervious to a switched off drill resulting in no virtual effects, and the haptic force applied to the user's tool would be in equilibrium to the force applied by the user.

Alternatively, the calculations can come out differently when the drill is switched on. For the switched on drill that is pressed against the bone, a different affordance set is presented.

Power Drill affordances (0.0-1.0)

[BluntPressure=0.00; SharpPressure=0.1; CuttingBlade=0.0; CuttingSaw=0.0; Drilling=0.75]

Using the same bone susceptibility values as outlined above, the same calculation is now as follows:

Damage Multiplier=(Drill SharpPressure Affordance*Bone(SharpPressure Susceptibility)+(Drill Drilling Affordance*Bone Drilling Susceptibility)

Damage Multiplier=(0.1*0.05)+(0.75*1.0)=0.7505

To reach the bone's Damage Threshold of 0.1, it can be seen that the user now has to apply (0.1/0.7505)=0.13 units of pressure.

The drill is therefore easily able to reduce and destroy bone voxels, and the maximum haptic force a bone could apply to the user's tool would be 13% of the initial pressure, giving a feeling of minimal resistance.

What is claimed is:

1. A computer based surgical training system, comprising
   (a) a processor;
   (b) a hand-held component operatively coupled to the processor and configured to provide a haptic feedback to a user;
   (c) a non-transitory computer readable storage medium encoded with a computer program that causes the processor to:
      (i) display a virtual object as part of a virtual surgical field, wherein the virtual object is associated with a susceptibility value and a damage threshold value;
      (ii) display a movement of a virtual surgical instrument within the virtual surgical field based on an input from the hand-held component when the user moves the hand-held component, wherein the virtual surgical instrument is associated with an affordance value;
      (iii) determine a damage multiplier value based on the susceptibility value and the affordance value;
      (iv) determine a haptic value by dividing the damage threshold value by the damage multiplier value; and
      (v) transmit the haptic feedback to the hand-held component, wherein a quantity of the haptic feedback that is transmitted is determined based on the haptic value.

2. The system of claim 1, wherein the hand-held component comprises a wand, a joystick, a mouse, a roller, a grasper, or a glove, wherein the hand-held component controls the virtual surgical instrument within the virtual surgical field, and wherein the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof.

3. The system of claim 1, wherein the virtual object comprises a representation of at least one of a bone, a muscle, an organ, a blood vessel, blood, or a nerve.

4. The system of claim 1, wherein the computer program further causes the processor to display a movement of the virtual surgical instrument in the virtual surgical field in the same direction as a movement of the hand-held component based on the input.

5. The system of claim 1, wherein the input comprises a force applied by the user to the handheld component, wherein the force corresponds to at least one of a gripping force, a pushing force, a pulling force, or a rotational force.

6. The system of claim 5, wherein the haptic feedback comprises a sensation that represents a response of the virtual object to the force.

7. The system of claim 1, wherein the haptic value comprises an algorithmic calculation of the susceptibility value and the affordance value.

8. The system of claim 7, wherein the algorithmic calculation corresponds to visual feedback comprising a visual effect on the virtual object.

9. The system of claim 1, wherein the movement comprises moving the virtual object with the virtual surgical instrument, cutting the virtual object with the virtual surgical instrument, applying a force to the virtual object with the virtual surgical instrument, or any combination thereof.

10. The system of claim 1, wherein the computer program causes the processor to: provide visual feedback corresponding to the movement.

11. The system of claim 10, wherein the visual feedback comprises a visual effect on the virtual object based on the susceptibility value, the input, and the affordance value.

12. The system of claim 11, wherein the visual effect comprises a deformation, a burning, a color change or discoloration, a clean cut, a minor cut, tearing or ripping, grinding, freezing, or any combination thereof.

13. The system of claim 10, wherein the visual feedback does not comprise a visual effect on the virtual object when the haptic value indicates the movement has no effect on the virtual object.

14. A computer implemented method comprising:
(a) displaying a virtual object as part of a virtual surgical field, wherein the virtual object is associated with a susceptibility value and a damage threshold value;
(b) displaying a movement of a virtual surgical instrument within the virtual surgical field based on an input from a hand-held component when a user moves the hand-held component, wherein the virtual surgical instrument is associated with an affordance value;
(c) determining a damage multiplier value based on the susceptibility value and the affordance value;
(d) determining a haptic value by dividing the damage threshold value by the damage multiplier value; and
(e) transmitting a haptic feedback to the hand-held component, wherein a quantity of the haptic feedback that is transmitted is determined based on the haptic value.

15. The method of claim 14, wherein the hand-held component comprises a wand, a joystick, a mouse, a roller, a grasper, or a glove, wherein the hand-held component controls the virtual surgical instrument within the virtual surgical field, and wherein the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof.

16. The method of claim 14, wherein the virtual object comprises a representation of at least one of a bone, a muscle, an organ, a blood vessel, blood, or a nerve.

17. The method of claim 14, wherein the input comprises a force applied by the user to the handheld component, wherein the force corresponds to at least one of a gripping force, a pushing force, a pulling force, or a rotational force.

18. The method of claim 17, wherein the haptic feedback comprises a sensation that represents a response of the virtual object to the force.

19. The method of claim 14, wherein the haptic value comprises an algorithmic calculation of the susceptibility value and the affordance value.

20. The method of claim 19, wherein the algorithmic calculation corresponds to visual feedback comprising a visual effect on the virtual object.

* * * * *